United States Patent [19]

Mekler

[11] Patent Number: 5,425,202
[45] Date of Patent: Jun. 20, 1995

[54] METHOD AND RECEPTACLES FOR GROWING PLANTS, PARTICULARLY TISSUE CULTURE PLANT PRECURSORS

[76] Inventor: Dan Mekler, Kore Hadorot 5, Jerusalem, Israel

[21] Appl. No.: 97,664

[22] Filed: Jul. 27, 1993

[30] Foreign Application Priority Data

Aug. 5, 1992 [IL] Israel .................................. 102741

[51] Int. Cl.⁶ .......................... A01B 79/00; A01C 1/00
[52] U.S. Cl. ............................................. 47/58; 47/85; 47/1.01
[58] Field of Search ........................ 47/1 A, 901, 58.01

[56] References Cited

U.S. PATENT DOCUMENTS

| | | |
|---|---|---|
| 3,903,643 | 9/1975 | Blackmore et al. ................... 47/1 A |
| 4,221,175 | 9/1980 | Van Wingerden et al. . |
| 4,620,390 | 11/1986 | Mekler . |
| 4,770,594 | 9/1988 | Hamilton ................... 47/1 A |
| 4,771,912 | 9/1988 | Van Wingerden ................... 47/1 A |
| 4,910,146 | 3/1990 | Tur-Kaspa et al. . |
| 5,215,550 | 6/1993 | Tesch, Jr. et al. ................... 47/1 A |

FOREIGN PATENT DOCUMENTS

| | | |
|---|---|---|
| 090474 | 10/1983 | European Pat. Off. . |
| 138611 | 4/1985 | European Pat. Off. . |
| 232628 | 8/1987 | European Pat. Off. . |
| 468381 | 1/1992 | European Pat. Off. . |
| 1230542 | 5/1986 | U.S.S.R. ................... 47/1 A |

Primary Examiner—Ramon S. Britts
Assistant Examiner—Joanne C. Downs
Attorney, Agent, or Firm—Ostrolenk, Faber, Gerb & Soffen

[57] ABSTRACT

A method of growing tissue culture callus on a nutrient substrate comprises the steps of preparing a semi-solid slab of the nutrient substrate and placing it on top of a honeycomb-like forming plate, which defines a plurality of hollow passages surrounded by thin walls. A series of the callus is deployed on the slab, so that each callus is located in alignment with one of the passages. The callus are allowed to grow to a desired extent under conventional conditions. A pneumatic pressure is then applied to the slab so that it becomes pushed through and sliced by the walls of the forming plate into a respective number of blocks, each carrying a single plant, and ejected out of the bottom side of the forming plate for further plantation thereof.

12 Claims, 6 Drawing Sheets

METHOD AND RECEPTACLES FOR GROWING PLANTS, PARTICULARLY TISSUE CULTURE PLANT PRECURSORS

BACKGROUND OF THE INVENTION

The present invention relates to breeding of plants and more particularly to plants breeding based on tissue culture cells or callus (hereinafter referred to as "callus") which are allowed to develop on a nutrient substrate, generally known as agar-agar.

The development of plant precursor on agar-agar base has rapidly increased, since found as the most effective way of plant cultivation, particularly due to the high yield (plants per area unit) that can be reached—in contradistinction to soil seed growing methods.

However, such callus growing, under laboratory condition, usually in test-tubes, bottles or similar containers, is disagreeable from the following aspects: The development of a plant, by its very nature, suffers if its surrounding is confined by partitions of any kind (impeding free growth in all directions; the "shadowing effect" of such partitions; and finally, the need to apply mechanical means (by the use of tweezers and the like) for extracting the plant for further cultivation thereof, usually re-planting thereof in seedling or transplantation trays. It is well-known that plants, at this early stage of their life, are most vulnerable so that transportation from one environment to another could be traumatic and therefore must be carried out with utmost care.

Various attempts have been proposed to partly solve this problem (see for example U.S. Pat. No. 4,620,390 to the present Applicant which is brought as general background).

It is thus the general object of the invention to provide a method of plant development ensuring, on the one hand, the free and unimpeded development of the callus in all directions and, on the other hand, the quick, convenient and least harmful translocation of the plants.

It is a further object of the invention to provide a method whereby the handling of the plants is effected without human touch, and which is readily performed by automatic means.

It is a still further object of the invention to provide a receptacle readily useful for carrying out the method of the present invention.

SUMMARY OF THE INVENTION

According to one, general aspect of the present invention there is provided a method of growing plants, particularly tissue culture callus grown on a nutrient substrate such as agar-agar. A semi-solid slab of the nutrient substrate is prepared and placed on top of a honeycomb-like forming plate, which defines a plurality of hollow passages surrounded by thin walls. A series of the callus is deployed on the slab, so that each callus is located in alignment with one of the passages. The callus are allowed to grow to a desired extent under conventional conditions. A pneumatic pressure is applied to the slab so that it becomes pushed through and sliced by the said walls into a respective number of blocks, each carrying a plant. The blocks are ejected out of the bottom side of the forming plate for further growing of the plants.

According to another aspect of the invention there is provided an assembly for growing plants, particularly tissue culture callus grown on a nutrient substrate such as agar-agar. The receptacle comprises a bottom tray, a forming plate comprising a honeycomb-like structure defining a plurality of hollow passages surrounded by thin walls and having a circumferential top and bottom frame walls. The bottom frame wall is configured to tightly fit into the bottom tray. A semi-rigid slab of a nutrient substrate is placed over the forming plate. A transparent cover tray is provided which fits over the forming plate.

BRIEF DESCRIPTION OF THE DRAWINGS

These and further aspects, advantages and features of the invention will become more clearly understood in the light of the ensuing description of a preferred embodiment of the invention, given by way of example only, with reference to the accompanying drawings, wherein.

DETAILED DESCRIPTION OF THE PREFERRED EMBODIMENTS

Figure 1:
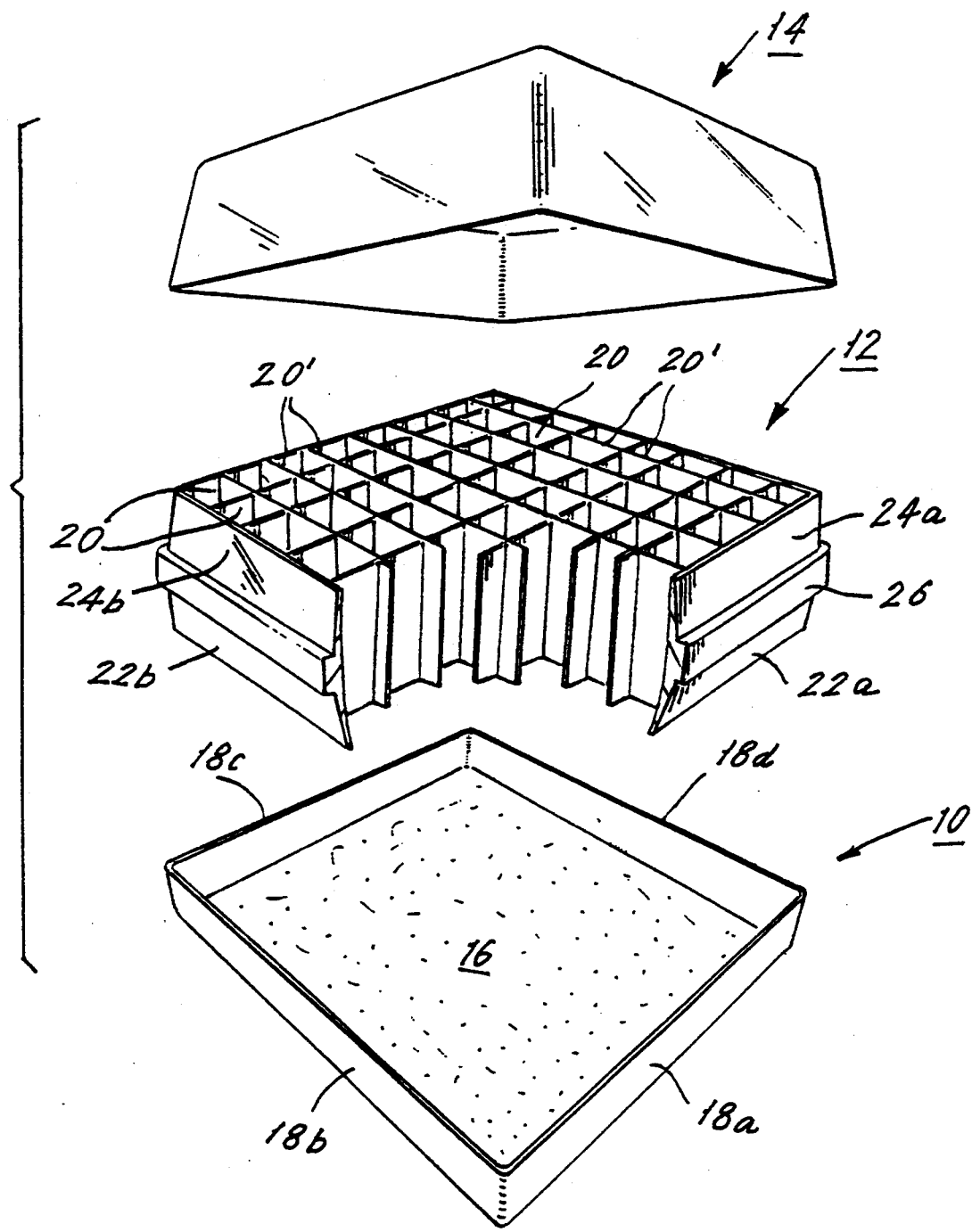
FIG. 1 is a three-dimensional, exploded view of the main components of a receptacle applicable for carrying out the method according to the present invention.
Figure 2:
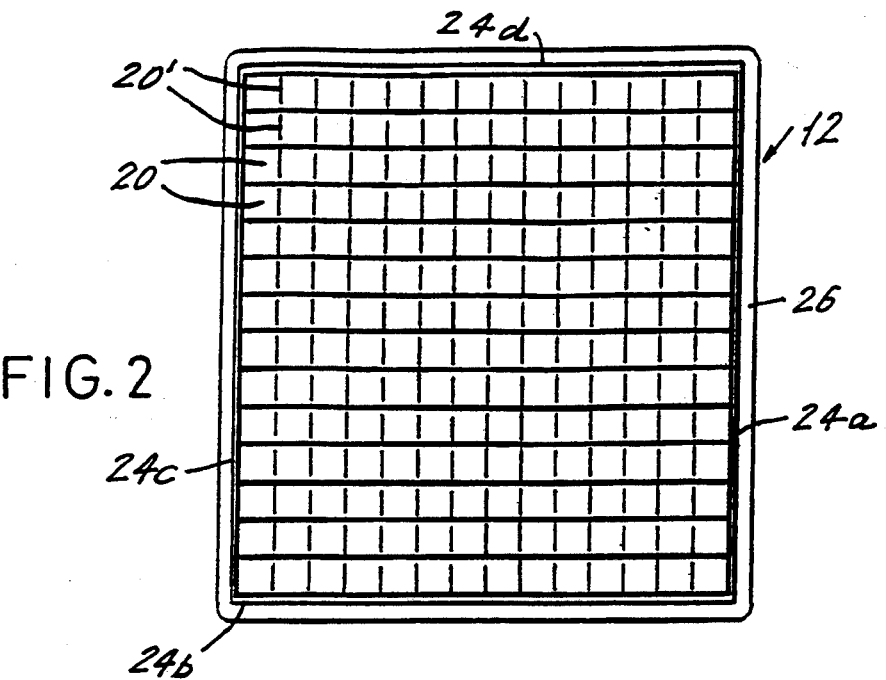
FIG. 2 is an elevation of the cellular forming plate shown in FIG. 1.

As shown in FIG. 1 the receptacle useful for the method provided according to the invention comprises a pan like tray 10, a honeycomb- or grid-like forming plate generally denoted 12, and a transparent cover tray designated 14. As shown, the base tray 10 is rectangular, although any other shape may be used as the requirements may dictate. The tray 10 has a bottom wall 16. Four side walls 18a, 18b, 18c and 18d are present, tapering outwardly to conform complementary walls of the forming plate 12 as will be described now.

The forming plate 12 is rectangular, conforming the dimensions of the tray 10, and comprises a grid structure defining cells or passages 20 of square cross-section. Again various other cross-section shapes may become useful. The passages 20 are divided by a lattice work of thin walls which preferably taper from bottom to top, ending with almost knife-edge lips 20' at the top side thereof. The plate is surrounded by four downwards convergent tapering circumferential bottom frame walls 22a–22d, four upwards convergent circumferential frame walls 24a–24d, and a girdle 26. The girdle may be continuous, or include various shaped sections. The frame walls 22 snugly fit into the open top of the base tray 10. Finally, the cover 14 fits over the walls 24, is necessarily transparent and of a sufficient height to make room for the growth of tissue culture callus as known in the art.

Figure 3:
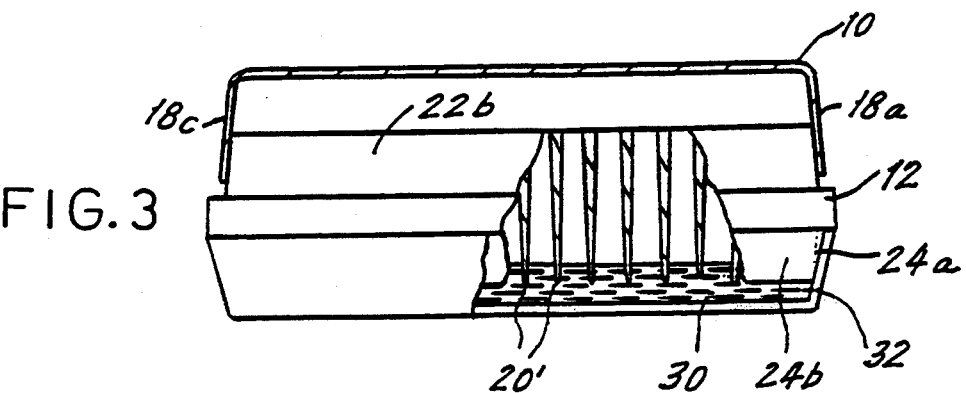
FIG. 3 is a partly cross-sectional view illustrating the stage of preparing a nutrient substrate slab with the forming plate partly embedded therein.

Turning now to FIG. 3 the stage of preparing a nutrient substrate slab for the planting of the live material callus is illustrated. As known, the nutrient substrate material ("agar-agar") is prepared from a solution of water and filler substances including minerals and other nutrient components necessary for the plant, which is molded into a suitable shape and allowed to solidify at room temperature to form a jelly like material.

According to one of the unique features of the invention, an agar-agar jelled slab, denoted 30, is prepared within a molding tray 32 which fits over the top frame wall 24 of the forming plate 12. Hence, the agar-agar, in liquid form, is poured into the tray 32 and the plate 12 is placed thereover so that the top, knife-edged lips 20' of the passages 20 are partly immersed and thus become embedded in the material of the slab after it solidifies. However, as will be explained later, this association between the forming plate 12 and the slab 30 is merely optional and the method provided according to the present invention can be put into practice without this feature.

Figure 4:
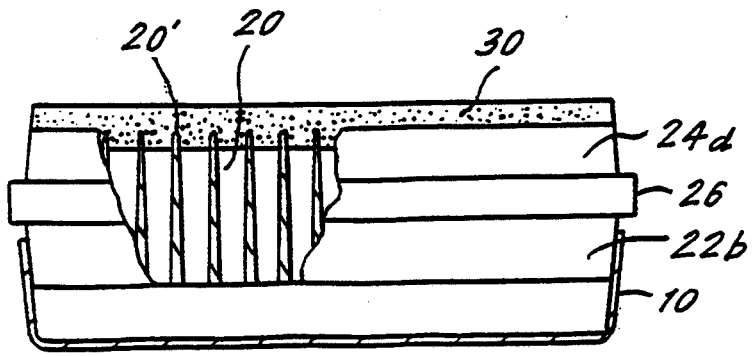
FIG. 4 illustrates a stage prior to the distribution of living matter, e.g. plant callus over the nutrient material slab.

After the solidification of the slab 30 and removal of the tray 32, the array comprised of the forming plate 12 with associated slab 30 and the bottom tray 10 is placed upside-down, as shown in FIG. 4.

Figure 5:
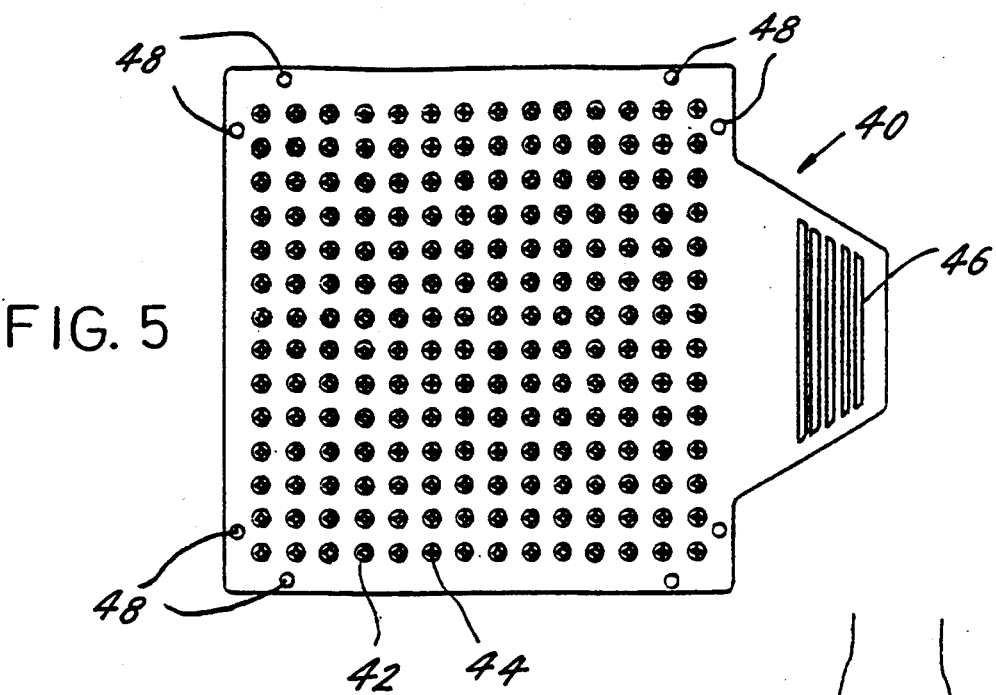
FIG. 5 illustrates a specifically designed strainer plate useful in carrying out the method according to the invention.
Figure 6:
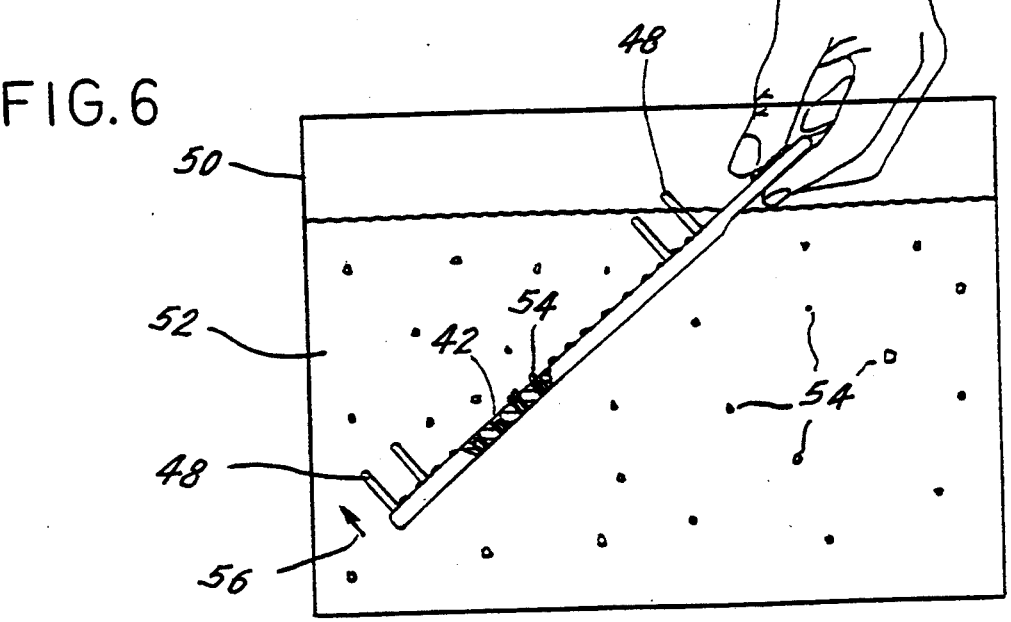
FIG. 6 illustrates the manner of spreading individual living material callus over the strainer plate.
Figure 7:
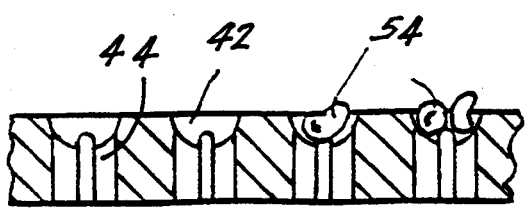
FIG. 7 shows, on an enlarged scale, a construction detail of the strainer plate.

Turning now to FIGS. 5, 6 and 7, there is shown a sift or strainer plate generally denoted 40 specially designed for facilitating the distribution or deploying of individual live matter bodies over the slab 30 in a predetermined, matrix arrangement, namely so that each body becomes located exactly over and in register with the center of each of the passages 20.

Figure 8:
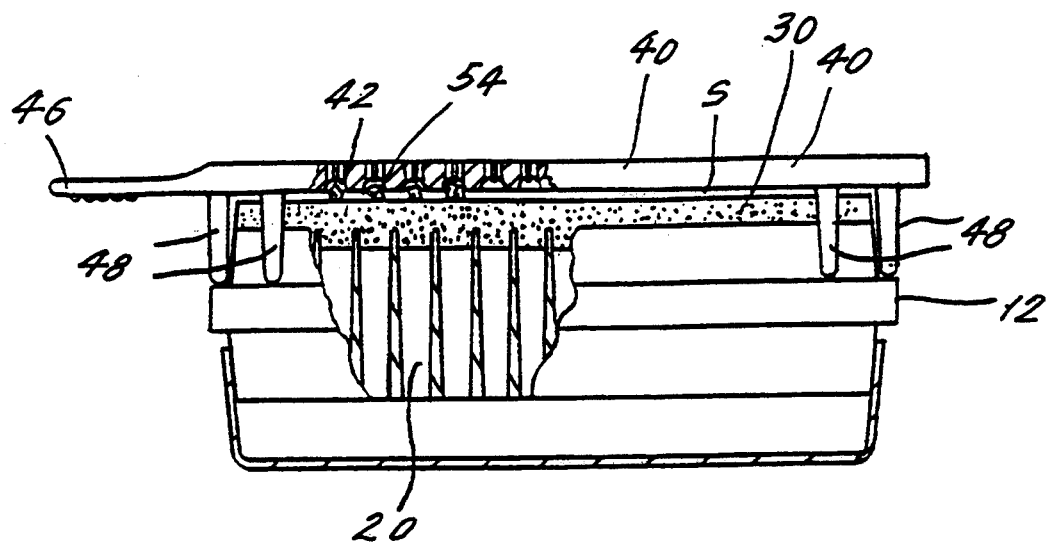
FIG. 8 illustrates the stage of transforming the living material callus over the nutrient substrate slab.

Thus, the plate 40 comprises a matrix of small depressions or recesses denoted 42 as most clearly shown in FIG. 7, extended by a draining or a dropping opening 44, preferably cross-shaped. Further provided is a handle portion 46 and eight location pins 48, each pair of location pins protrude from the side of the depressions extending at the four corners of the strainer plate 40, the arrangement being such that when the plate 40 is placed over the forming plate 12 all the depressions 42 become located in alignment with a central axis of the respective passages 20, as well as at a certain distance S above the slab 30—as clearly shown in FIG. 8.

The process of placing individual living material callus into the depressions 42 is illustrated in FIG. 6 and performed in the following manner. There is prepared a container 50 filled with a liquid 52 wherein individual live material callus 54 are distributed and hold in suspension. Now, by passing the plate 40 through the liquid 52 in upwards movement, as denoted by the arrow 56, callus 54 are individually "fished" and become entrapped within the depressions 42 (see in FIG. 7).

A similar result can be achieved by pouring a liquid suspension such as 52 over and through the strainer plate 40.

Figure 9:
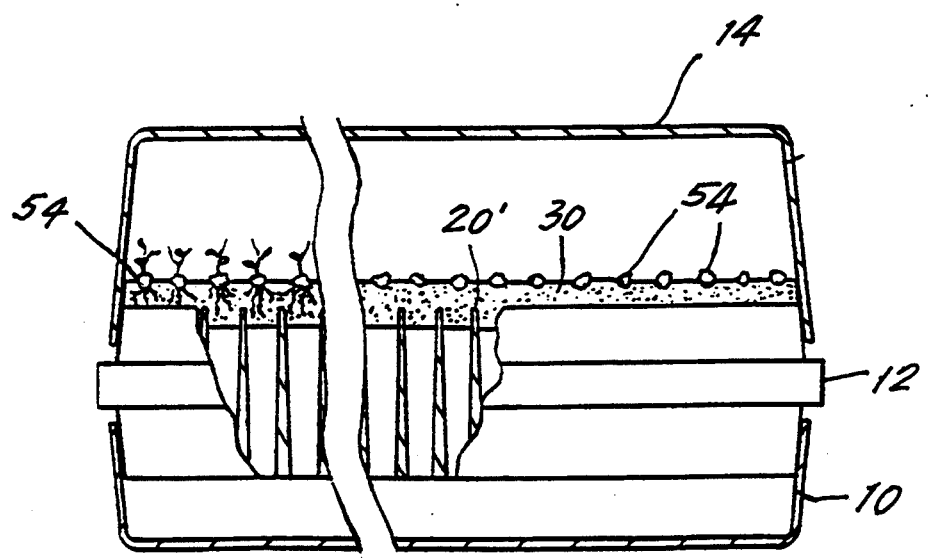
FIG. 9 illustrates at its right hand side, the planted living matter callus, and at its left hand side, plants at their final developed stage.

The strainer plate 40, charged with the callus 54 (although some of the depressions 42 may be left vacant), must now be loaded onto the slab 30. For this purpose the assembly of the bottom tray 10 and the forming plate 12 (FIG. 4) is placed in an upside-down position over the strainer plate 40 (not shown), and then turned over together back into the position shown in FIG. 8. Removal of the strainer plate 40 will leave the callus 54 lying on the slab 30 as shown in FIG. 9. A further operation of sticking the callus 54 partly into the material of the slab 30 may be necessary and manually performed with a suitable tool (not shown).

The transparent cover plate 14 is now placed over the forming plate 12 and the plants are allowed a grow up to a suitable size (about 10 mm) as designated 56 in the left hand side of FIG. 9.

Figure 10A:
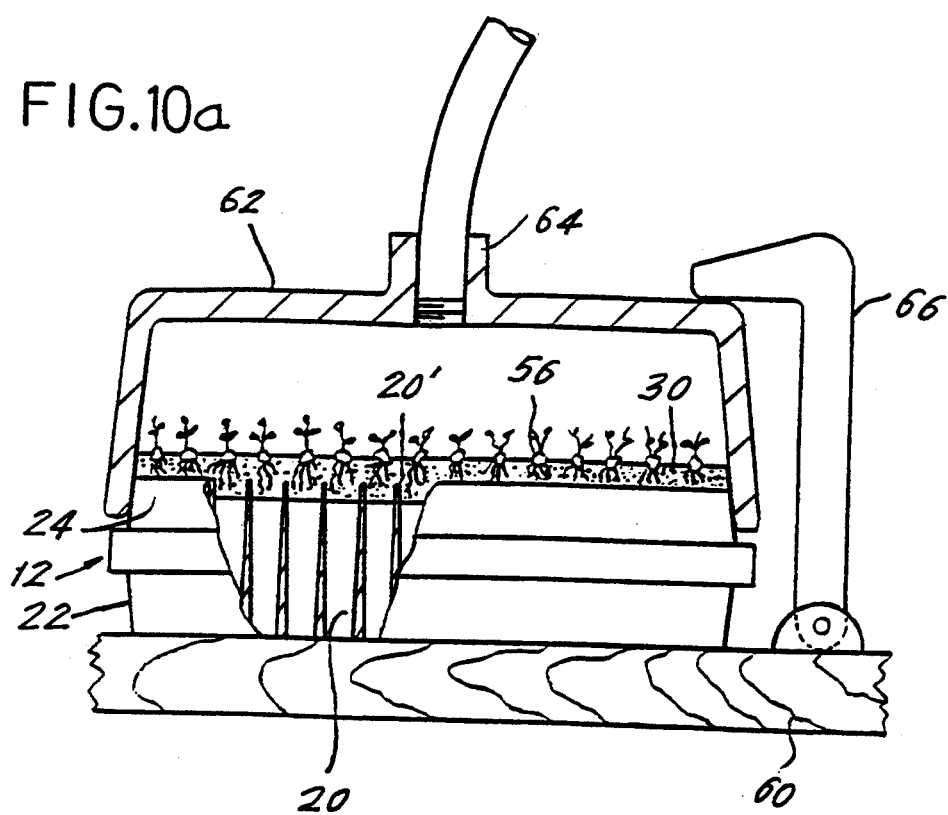
FIGS. 10a and 10b illustrate the slicing stage of the nutrient substrate slab.
Figure 10B:
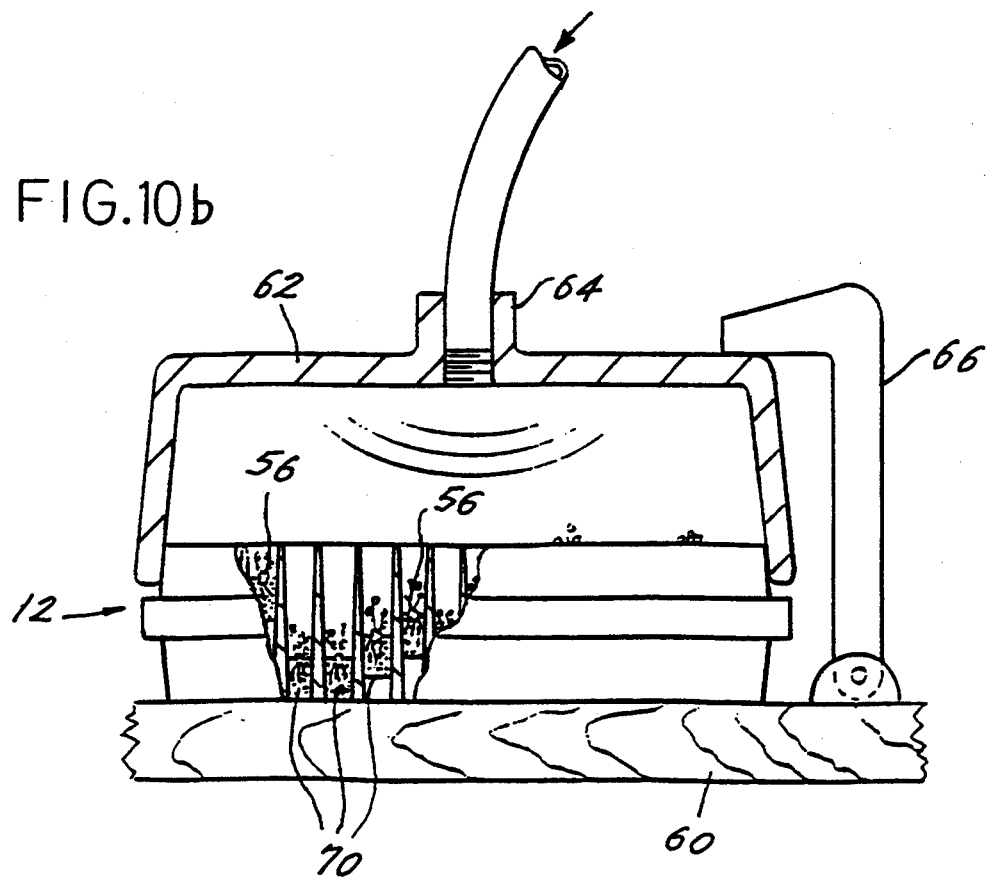

In order to remove the plants 56 out of the receptacle for the following transplantation thereof, say into conventional plantation trays, the process illustrated in FIG. 10a and 10b is performed. The forming plate 12 is placed over a base 60 after it is removed from the base tray 10. The top surface of the base 60 is preferably made rough to allow the venting of air (see below). An additional cover tray 62, with air pressure fitting 64, is placed tightly over the upper frame walls 24 of the plate 12 and preferably clamped thereto by a pivoted hook member 66.

Now, by applying sufficient air pressure into the cover tray 62, the slab 30 functions as a "plunger" and becomes pushed downwards as a unitary body, causing thereby the gradual slicing thereof by the edges 20' of the respective passages 20. The slab thus becomes divided into square blocks 70, each ultimately seated against the base 60 at the bottom side of the tray 12, including its respective plant 56 (see FIG. 10b).

The system is now ready for the final stage of ejecting the blocks 70 outwards through the open bottom of each passage 20. This operation can be performed by again using air pressure delivered through one or more nipples 72 fitting into the top of passage(s) 20.

Figure 11:
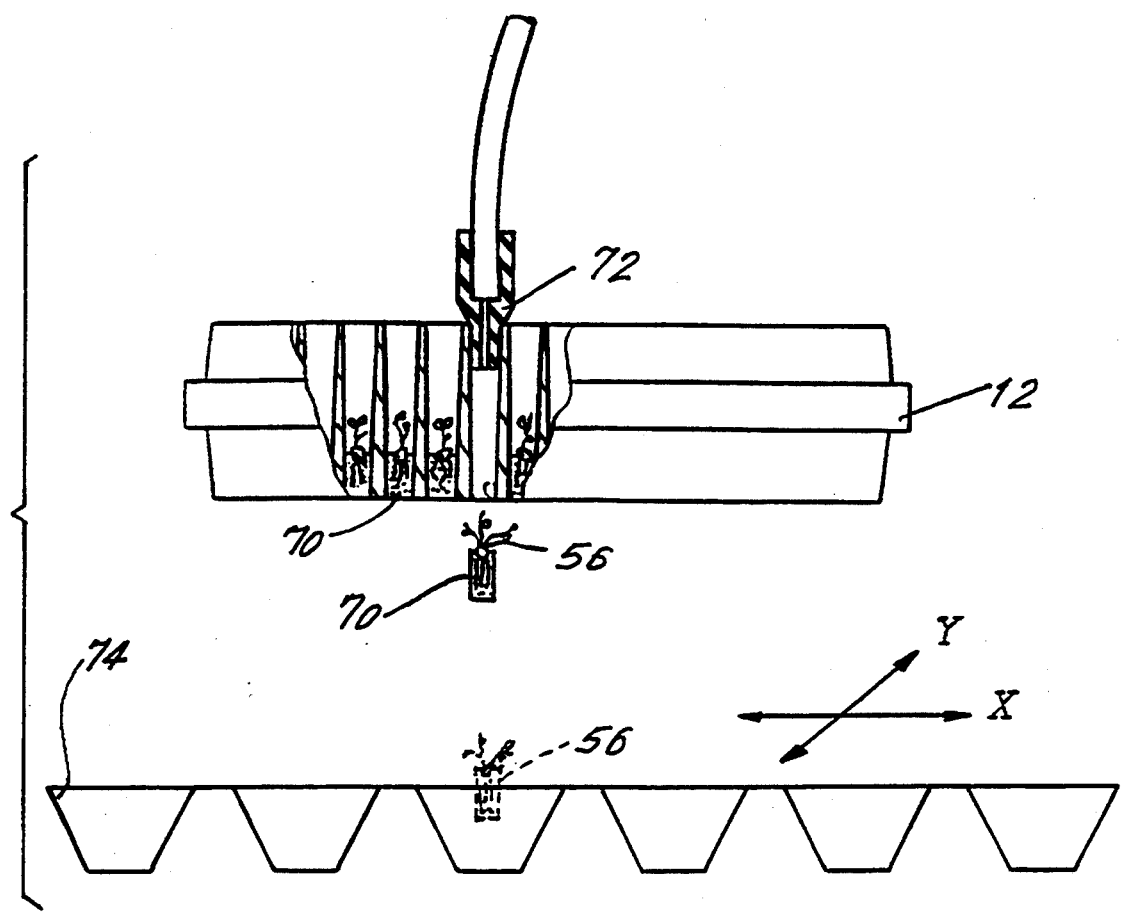
FIG. 11 illustrates the manner of ejecting individual plants together with their associated blocks of the slab, for further processing.

It will be readily appreciated that the plants 56 may be now further processed, by automated machinery (not shown), directing each and every block 70 into a respective compartment of a conventional transplantation tray 74 moving in the X-Y directions as schematically illustrated in FIG. 11.

It has been thus shown that by relatively simple and straightforward equipment, an advantageous method is provided, ensuring a convenient, quick and effective live tissue growing of plants which, on the one hand, guarantees minimum traumatic damage to the so sensitive tiny plants at the end of their development, and on the other hand, is readily applicable for following processing and handling techniques.

Those skilled in the art will readily appreciate that numerous changes, variations and modifications may be applied to the invention as heretofore exemplified without departing from the scope thereof as defined in and by the appended claims.

What is claimed is:

1. A method of growing plants, particularly tissue culture callus grown on a nutrient substrate such as agar-agar, comprising the steps of:
   preparing a semi-solid slab of the nutrient substrate,
   placing the slab on top of a honeycomb-like forming plate, defining a plurality of hollow passages surrounded by thin walls,
   deploying a series of the callus onto the slab, so that each callus is located in alignment with one of the passages,
   allowing the callus to grow to a desired extent under conventional conditions, applying a pneumatic pressure to the slab so that it becomes pushed through and sliced by the said walls into a respective number of blocks, each carrying a plant, and ejecting the blocks out of the bottom side of the forming plate.

2. The method as claimed in claim 1 wherein the slab is molded in a pan-like tray while the top side of the said forming plate is partly embedded in the material of the slab.

3. The method as claimed in claim 2 wherein the walls of the forming plate taper convergently toward the top side thereof.

4. The method as claimed in claim 3 wherein the forming plate includes convergent tapered top and bottom circumferential frame walls, and a girdle therebetween.

5. The method as claimed in claim 4 wherein the forming plate fits into an open top base tray.

6. The method as claimed in claim 1 wherein the said deploying of the callus onto the slab comprises the steps of:

preparing a liquid medium containing the said callus in suspension, providing a strainer-like plate with a matrix of depressions, each extended by a drain opening, the arrangement of the matrix thereof conforming the said aligned locations relative to the forming plate passages upon stacking the strainer plate thereover, passing the strainer plate through the liquid suspension so that callus become entrapped each within one of the said depressions, and laying the series of callus over the top surface of the said slab without changing their relative positions.

7. The method as claimed in claim 6 wherein the strainer plate is provided with location means adapted to cooperate with a circumferential frame wall of the forming plate.

8. The method as claimed in claim 7 wherein the said location means comprises a series of pins projecting from the said strainer plate.

9. The method as claimed in claim 6 wherein the said drain openings are of a cross-shape cross-section.

10. The method as claimed in claim 6 wherein the said laying of the callus over the slab comprises the step of placing the slab over the strainer plate and turning both upside-down.

11. The method as claimed in claim 1 wherein the said blocks are ejected from their respective passages by applying air pressure into the passage.

12. The method as claimed in claim 11 wherein the said blocks are ejected into respective compartments of a transplantation tray.

* * * * *